(12) United States Patent
Clement et al.

(10) Patent No.: US 7,731,734 B2
(45) Date of Patent: Jun. 8, 2010

(54) VERTEBRAL OSTEOSYNTHESIS EQUIPMENT

(75) Inventors: Jean-Luc Clement, La Colle sur Loup (FR); Vincent Fiere, Lyons (FR); Jean Taylor, Cannes (FR); Yves Adam, Authie (FR); Bernard Villaret, Croix-Chapeau (FR)

(73) Assignee: Medicrea Technologies, La Rochelle (FR)

( * ) Notice: Subject to any disclaimer, the term of this patent is extended or adjusted under 35 U.S.C. 154(b) by 221 days.

(21) Appl. No.: 10/561,509

(22) PCT Filed: Jun. 24, 2004

(86) PCT No.: PCT/IB2004/002463

§ 371 (c)(1),
(2), (4) Date: Apr. 18, 2006

(87) PCT Pub. No.: WO2005/000137

PCT Pub. Date: Jan. 6, 2005

(65) Prior Publication Data

US 2006/0229606 A1    Oct. 12, 2006

Related U.S. Application Data

(60) Provisional application No. 60/490,519, filed on Jul. 29, 2003.

(30) Foreign Application Priority Data

Jun. 27, 2003  (FR) .................................. 03 07776
Jan. 27, 2004  (FR) .................................. 04 00747
Apr. 1, 2004   (FR) .................................. 04 03413

(51) Int. Cl.
*A61B 17/70* (2006.01)

(52) U.S. Cl. .................. 606/246; 606/264; 606/266
(58) Field of Classification Search ............ 606/61, 606/266, 253, 256, 257, 267, 268, 271, 274; 403/132, 134, 138
See application file for complete search history.

(56) References Cited

U.S. PATENT DOCUMENTS

| | | | | | |
|---|---|---|---|---|---|
| 4,946,458 | A | * | 8/1990 | Harms et al. | 606/61 |
| 5,254,118 | A | * | 10/1993 | Mirkovic | 606/61 |
| 5,380,325 | A | * | 1/1995 | Lahille et al. | 606/61 |
| 5,549,690 | A | * | 8/1996 | Hollister et al. | 623/21.15 |

(Continued)

FOREIGN PATENT DOCUMENTS

EP          0 242 708        10/1987

(Continued)

*Primary Examiner*—Thomas C Barrett
*Assistant Examiner*—Nicholas Woodall
(74) *Attorney, Agent, or Firm*—Young & Thompson

(57) ABSTRACT

Equipment includes bony anchoring members, one or two linking rods, intended to be connected to these anchoring members, and parts for connecting the rod(s) to the anchoring members; at least one anchoring member includes a proximal stud articulated with respect to a base portion enabling bony anchoring; clamping elements enable assembly of the connecting part on the anchoring member. The proximal stud includes a surface forming an axial stop, against which the connecting part is intended to rest, and the clamping elements clamp this connecting part against this surface which is positioned so that the connecting part, when clamped there against, is not clamped against the base portion so that there remains, after clamping, a possibility of articulated backlash of the proximal stud with respect to the base portion.

14 Claims, 3 Drawing Sheets

U.S. PATENT DOCUMENTS

| | | | |
|---|---|---|---|
| 5,613,968 A * | 3/1997 | Lin .................................. | 606/61 |
| 5,672,175 A * | 9/1997 | Martin ............................. | 606/61 |
| 5,735,851 A | 4/1998 | Errico et al. | |
| 5,800,435 A * | 9/1998 | Errico et al. .................... | 606/61 |
| 5,938,663 A * | 8/1999 | Petreto ............................ | 606/61 |
| 6,050,997 A * | 4/2000 | Mullane .......................... | 606/61 |
| 6,123,706 A * | 9/2000 | Lange ............................. | 606/61 |
| 6,267,765 B1 * | 7/2001 | Taylor et al. .................... | 606/86 A |
| 6,554,831 B1 * | 4/2003 | Rivard et al. ................... | 606/61 |
| 2003/0028191 A1 * | 2/2003 | Shluzas .......................... | 606/61 |
| 2003/0073996 A1 * | 4/2003 | Doubler et al. ................ | 606/61 |
| 2005/0165396 A1 * | 7/2005 | Fortin et al. .................... | 606/61 |

FOREIGN PATENT DOCUMENTS

| | | |
|---|---|---|
| FR | 2 697 742 | 5/1994 |
| WO | WO 91/06254 | 5/1991 |
| WO | WO 98/55038 | 12/1998 |
| WO | WO 03/007828 A1 * | 1/2003 |

* cited by examiner

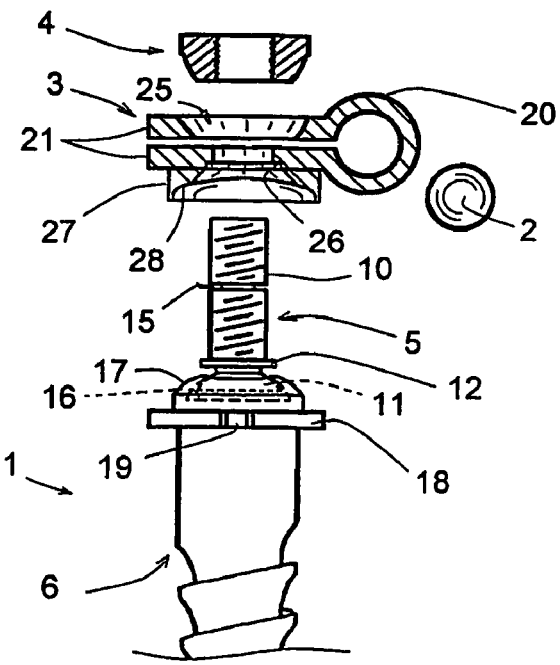
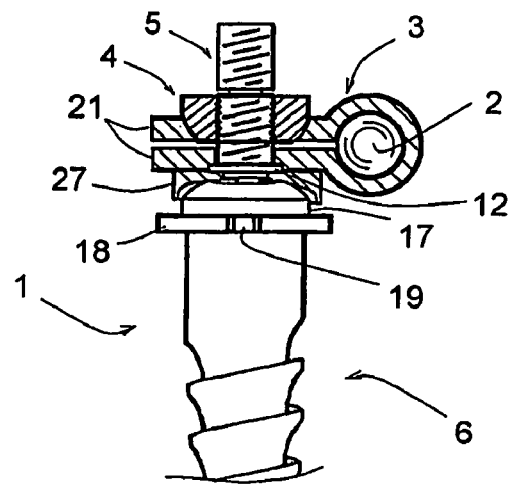
FIG. 1
FIG. 2
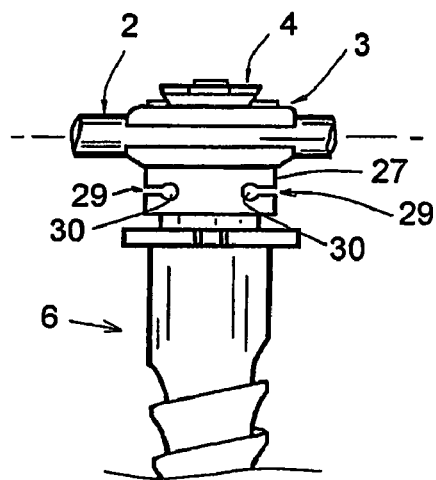
FIG. 3
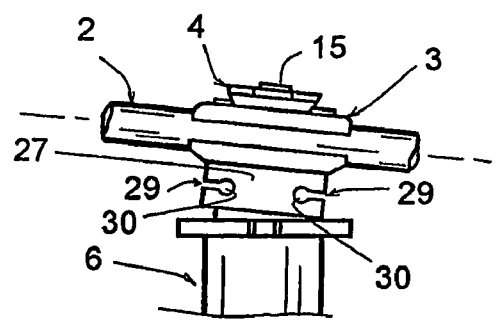
FIG. 4
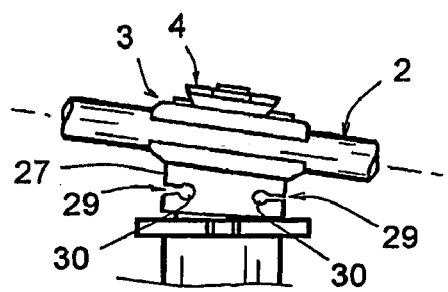
FIG. 5

VERTEBRAL OSTEOSYNTHESIS EQUIPMENT

This patent application claims the priorities to:
FR 03 07776, filed on Jun. 27, 2003;
U.S. Provisional application No. 60/490,519, filed on Jul. 29, 2003;
FR 04 00747, filed on Jan. 27, 2004;
FR 04 03413, filed on Apr. 1, 2004.

The present invention relates to a vertebral osteosynthesis equipment.

A vertebral osteosynthesis equipment generally includes bony anchoring members, such as pedicular screws and/or hooks, one or two linking rods, intended to be connected to these anchoring members and to be attached to the vertebrae by dint thereof, and parts for connecting this(these) linking rod(s) to these anchoring members. The equipment may also comprise length-adjustable crossbeams, which link transversally two parallel linking rods in order to hold said rods with respect to one another.

In an existing type of equipment, at least one anchoring member is "polyaxial", i.e. comprises a base portion enabling bony anchoring thereof and a proximal threaded stud, articulated with respect to that base portion, whereon a nut may be screwed. Each connecting part may comprise a rounded section intended for surrounding a linking rod and two parallel drilled wings, these wings being intended for engaging onto said proximal threaded stud and for being clamped, by means of that nut, against a bearing surface provided on the base portion, said operation enabling to clamp said rounded section around the linking rod and thereby ensuring longitudinal immobilisation of this rod with respect to the anchoring member.

The existing vertebral osteosynthesis equipment is designed for immobilising two vertebrae with respect to one another, for eliminating any relative movement of these vertebrae, liable to be painful, or to restore the adequate position of a vertebra with respect to the other. To provide such immobilisation, such equipment is designed for ensuring perfectly rigid assembly of the linking rods with the anchoring members.

Such rigid assembly may however not prove desirable in all cases. It leads in particular to significant loads being exerted at anchoring bony zones of said anchoring members, as well as to increased loads at the vertebral articulations situated on both sides of the vertebral segment(s) treated, which may lead to precocious degenerescences of these articulations.

It is known by the document U.S. Pat. No. 5,735,851 to provide a polyaxial anchoring member whereof the proximal threaded stud may accommodate one or several concave spacers screwed thereon, these spacers being intended for resting against the convex head of the base portion of the anchoring member. The function of these spacers, besides adjusting the height of the connecting part, is to generate an additional clamping load on the head of the base portion in order to enhance the immobilisation of the stud with respect to that base portion after clamping.

The anchoring member according to this prior document realises consequently a rigid assembly of the stud with respect to the base portion, which does not enable to remedy the shortcomings aforementioned.

The document FR 2 697 742 describes a monoaxial anchoring member including a washer made of shock-absorbing material placed between a bearing surface formed by the base portion and the connecting part. The clamping nut immobilises however this connecting part with respect to the proximal threaded stud of the anchoring member, and said washer only enables very limited movements of the connecting part with respect to the anchoring member.

The equipment according to this prior document also realises consequently a rigid or quasi-rigid assembly which does not enable to remedy the shortcomings aforementioned.

The purpose of the present invention is precisely to remedy these shortcomings.

The equipment affected comprises, in itself, bony anchoring members, such as pedicular screws and/or hooks, one or two linking rods, intended to be connected to these anchoring members, and parts for connecting this(these) rod(s) to these anchoring members; at least one of the anchoring members is of the "polyaxial" type, i.e. it comprises a proximal stud articulated with respect to a base portion enabling bony anchoring; clamping means enable assembly of the connecting part on the anchoring member.

According to the invention, the proximal stud comprises a surface forming an axial stop, against which the connecting part to be installed on the polyaxial anchoring member is intended for resting, and said clamping means enable to clamp this connecting part against this surface, said surface being positioned so that the connecting part, when it is clamped against this surface, is not clamped against the base portion so that there remains, after clamping, a possibility of articulated backlash of the proximal stud with respect to said base portion.

Thus, in the equipment according to the invention, said connecting part is not immobilised with respect to the anchoring member but may move slightly, relative thereto, in order to allow limited movements of the vertebrae. The stresses exerted on the anchoring bony zones of the anchoring member are thus notably reduced, as well as the risks of overstresses at the vertebral articulations situated on both sides of the vertebral segment treated.

Preferably, at least one polyaxial anchoring member comprises at least one part or portion of a part with elastically deformable structure, interposed, after assembly, between said connecting part and a bearing surface.

This part or portion of a part with elastically deformable structure enables to dampen the movement of the connecting part, and hence of the linking rod, with respect to said base portion. Thanks to the axial stop surface shown by the stud, the clamping of the connecting part is carried out independent of any clamping of said part or portion of a part, which is elastically deformable, and hence does not interfere therewith.

Said part or portion of a part with elastically deformable structure may be formed in order to dampen the movement of the proximal stud over the whole backlash of this stud, notably if it is composed of a compressible material, or may be formed to provide this dampening effect only in the extreme positions of such backlash.

According to a possible embodiment of the invention in the latter case, said part or portion of a part with elastically deformable structure is composed of a circular wall attached to the connecting part, this wall including at least one transversal slot running therethrough, provided on one side of this wall according to a direction substantially perpendicular to that occupied by a linking rod when this rod is engaged in the connecting part, this slot enabling to reduce the thickness of this circular wall when a load is exerted on this wall in the axial direction, on the side where the slot is.

The proximal stud and said surface forming an axial stop may be formed in order to enable the adjustment of the axial position of this surface with respect to the proximal stud, and this surface may be formed to clamp said part or portion of a part with elastically deformable structure between said surface and said bearing surface against which this part or portion of a part rests.

Said surface forming an axial stop enables then, according to the clamping performed, to adjust the dampening effect produced by said part or portion of a part with elastically deformable structure.

According to an embodiment of the invention in such a case, the proximal stud is threaded and said surface forming an axial stop is in the form of a part with a tapered hole which may be screwed on this stud.

Said bearing surface against which the part or portion of a part with elastically deformable structure rests, may be a surface provided on said base portion or the vertebral bone itself.

The walls of the proximal stud and of the anchoring member which slip against one another during the backlash of this stud may include a smooth and resistant coating layer, capable of resisting a very large number of slipping movements of these walls against one another, such as a ceramic or titanium nitride coating layer.

When the articulation of this proximal stud consists of faces in the form of a sphere or of portions of a sphere slipping against one another, advantageously, these faces exhibit a diameter which is significantly greater than that of the proximal stud, notably at least double the diameter of this stud, in order to increase the contact surface of its faces with one another.

The frictions are thus exerted on enlarged surfaces, thereby reducing the risk of wear of said faces.

Besides, at least one linking rod of the equipment may comprise:
  a portion of rod including a part with elastically deformable structure and an articulated stud,
  another portion of rod including a bearing zone against this part with elastically deformable structure, and
  clamping means to clamp this bearing zone against this part with elastically deformable structure.

The connecting part comprises preferably a rounded section intended for surrounding a linking rod and two parallel drilled wings, intended for engaging onto said proximal stud and for being clamped towards one another in order to provide the clamping of said rounded section around a linking rod.

The invention will be better understood, and other characteristics and advantages thereof will appear, with reference to the appended schematic drawing, representing, for non-limiting exemplification purposes, two embodiments of parts included in the equipment affected.

FIG. 1 is one of these parts, before assembly, according to an embodiment;

FIG. 2 is a view of these parts similar to FIG. 1, after assembly;

FIG. 3 is a view of these parts similar to FIG. 2, according to a direction perpendicular to that according to this FIG. 2, in a first position;

FIG. 4 is a view of these parts similar to FIG. 3, in a second position;

FIG. 5 is a view of these parts similar to FIG. 3, in a third position;

Figure 6:
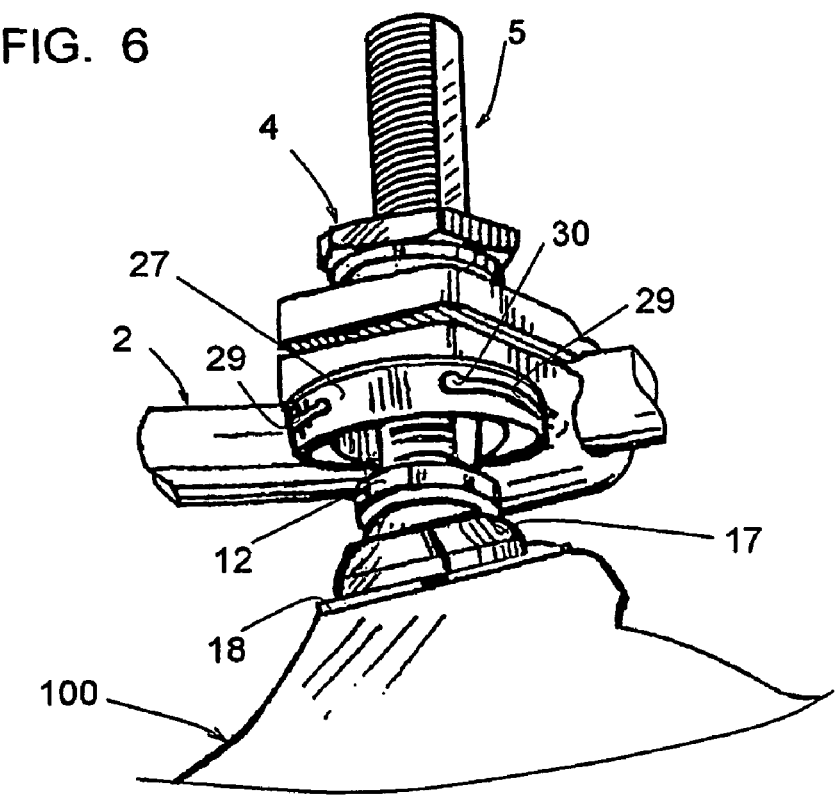
FIG. 6 is a perspective view of the same parts, after placing the screw in a vertebra and before final clamping.

FIG. 1 represents a polyaxial pedicular screw 1, a rod 2 linking several of these screws 1, a part 3 connecting this rod 2 to one of these screws 1 and a nut 4 enabling to assemble the linking rod 2 to this screw 1.

Figure 7:
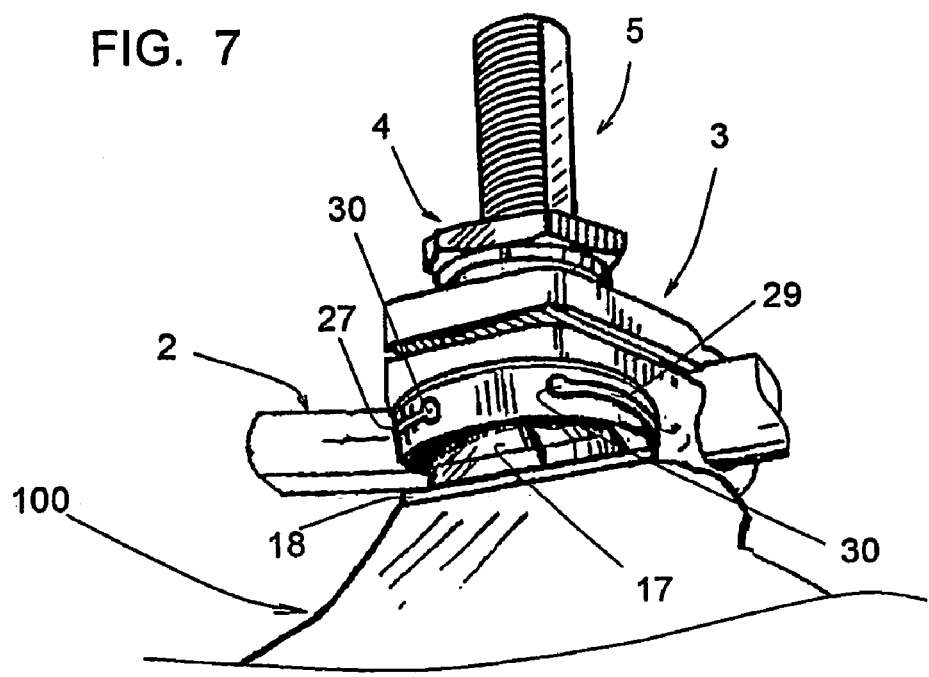
FIG. 7 is a view of these parts similar to FIG. 6, after final clamping.

The screw 1 comprises a proximal threaded stud 5 and a threaded base portion 6. The stud 5 is intended for receiving the part 3 engaged thereon and the nut 4 screwed thereon while the body 6 is intended for insertion in the pedicula 100 of a vertebra, as shown on FIGS. 6 and 7.

The stud 5 exhibits a threaded cylindrical portion 10, an enlarged distal head 11 and a collar 12 forming a stopping surface.

The portion 10 exhibits a zone 15 of reduced diameter, enabling to break its proximal portion after placing and clamping the nut 4, as appears by comparison of FIGS. 2 and 3.

The head 11 exhibits a diameter double the diameter of the portion 10 and looks like a spherical cap. This head 11 is intended for engaging in a proximal cavity 16 delineated by the proximal zone of the body 6 and for retention in this cavity 16 by crimping a proximal wall 17 exhibited by this body 6. After crimping, the wall 17 is shaped in order to show a hemispherical proximal form. As shown on FIG. 1, the dimensions of the cavity 16 and of the aperture delineated by the wall 17 after crimping to let through the stud 5 are such that a multidirectional backlash of this stud 5 with respect to the body 6 is possible.

The body 6 also comprises a proximal collar 18, intended for abutting against the pedicula 100. This collar 18 exhibits several radial notches 19, notably four notches at 90° to one another, for holding the body 6 in rotation when clamping the nut 4.

The linking rod 2 is cylindrical and exhibits such rigidity as to hold several vertebrae with respect to one another. This rod 2 is however deformable in order to be shaped relative to the correction of the rachis to be performed.

The connecting part 3 comprises a rounded section 20 intended for surrounding the linking rod 2 and two parallel lateral wings 21 drilled with holes for engaging the part 3 on the stud 5. These wings 21 are distant mutually so that, in a distant position, the rod 2 may be inserted and may slide in the portion 20, and that, in a close position provided by the clamping of the nut 4, they clamp the portion 20 around the rod 2, immobilising the latter with respect to the part 3.

As shown on FIGS. 1 and 2, the proximal wing 21 exhibits a proximal pan 25 whereof the shape is suitable for the nut 4 to rest on, while the distal wing 21 comprises a circular cavity 26 enabling the engagement of this wing on the collar 12.

This distal wing 21 comprises moreover a circular wall 27 integral therewith. The height of this wall 27 is smaller than that of the wall 17, and delineates an internal concave spherical face 28 of greater diameter than that of this wall 17.

Moreover, two transversal slots 29 are provided in this wall 27, on two opposite sides of the wall 27, and according to a direction substantially perpendicular to that occupied by the linking rod 2 when this rod is engaged in the rounded section 20. Each slot 29 extends angularly over approximately 120° of the wall 27 and terminated by a widened zone 30 in the form of a circle.

As can be understood with reference to FIG. 5, the distal portions of the wall 27 delineated by the slots 29 have, at these rounded zones 30, reduced height, so that these portions may flex at these zones 30, enabling thereby reduction in height of the wall 27.

In practice, the number of screws 1 necessary to the treatment to be performed is placed in the pediculae 100 of the vertebrae affected, then the connecting parts 3, with the rod 2 engaged in the portions 20, are placed on the studs 5, until engagement of the collars 12 in the cavities 26. The nuts 4 are then clamped to immobilise the rod 2 with respect to the parts 3 and the proximal portions of the studs 5 are cut off.

In this clamping position of each part 3 against the corresponding collar 12, the wall 27 only rests against the wall 17 by a very small surface, as shown on FIG. 2. This clamping preserves the possibility of articulated backlash of the proximal stud 5 with respect to the body of screw 6, this backlash being free as long as the wall 27 has not abutted against the body 6 (cf. FIG. 4) then being possible with a deformation of the wall 27 beyond, thereby dampening the movement of the stud 5 in the maximal angles of backlash of this stud (cf. FIG. 5). The possible limit of the backlash of the latter corresponds to the contact of the edges of the wall 27 delineating the slots 29.

Thanks to the diameter of its face 28, greater than the diameter of the wall 17, the wall 27 does not oppose the backlash of the stud 5.

The slipping zones of the head 11 against the wall 17 and of the face 28 against the wall 17 may include a smooth and resistant coating layer, capable of resisting a very large number of slipping movements of these walls against one another, such as a ceramic or titanium nitride coating layer.

Figure 8:
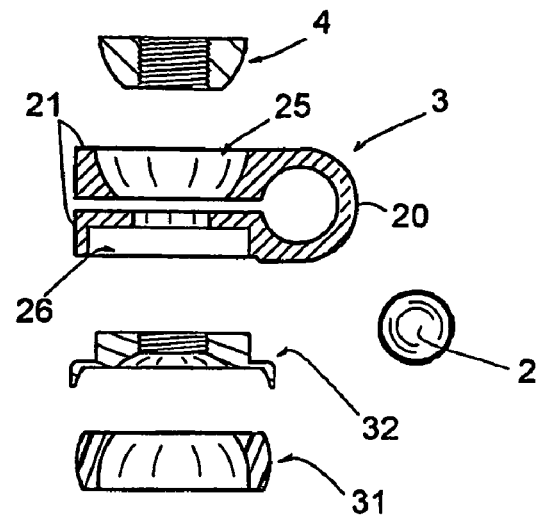
FIG. 8 is a view of said parts, before assembly, according to the second embodiment.
Figure 8:
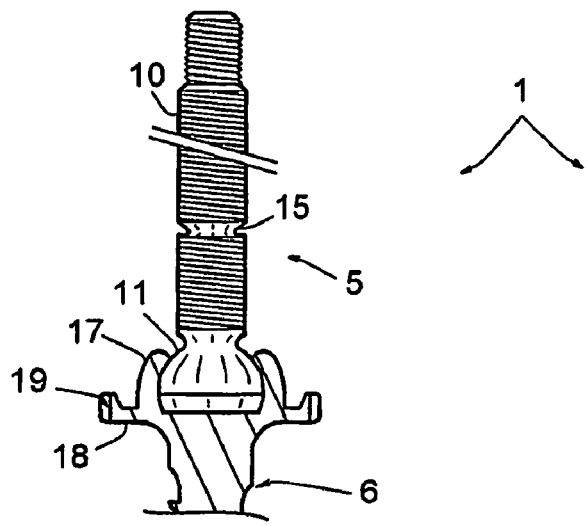
Figure 9:
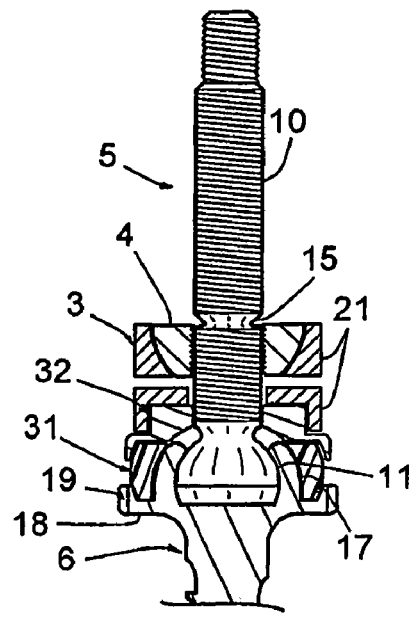
FIG. 9 is a view of said parts similar to FIG. 8, after assembly.

FIGS. 8 and 9 represent parts 2 to 4 identical or similar to those described with reference to FIGS. 1 and 2, the parts proving identical or similar being designated by the same numeric references.

In this case, the part 3 is deprived of the wall 27, and the equipment comprises, for at least one anchoring member 1, a part 31 in the form of a washer made of material with elastically deformable structure, notably silicon or PMMA, and a washer 32, notably metallic, with a tapered bore to be screwed on the stud 5 until the part 31 is clamped between said washer and the portion 6 of the screw.

The part 31 delineates a cavity as a portion of a sphere, of dimensions adjusted to the external face of the wall 17.

The washer 32 comprises an upper portion adjusted to the cavity 26 and a lower widened portion, including a peripheral rim which may be engaged on the upper portion of the washer 31, as shown on FIG. 9.

This washer 32 may be screwed on the stud 5 until the part 31 is clamped relative to a given dampening effect requested for the backlash of the stud 5. Once such clamping has been provided, the part 3, with the rod 2 engaged therein, is placed on the stud 5, then the nut 4 is clamped to immobilise the rod 2 with respect to the part 3.

Figure 10:
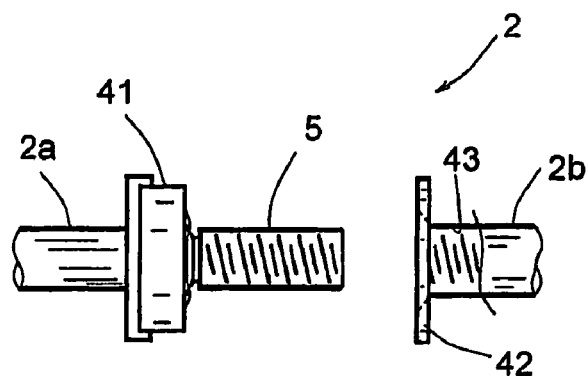
FIG. 10 is a partial sectional view of a linking rod, before assembly.
Figure 11:
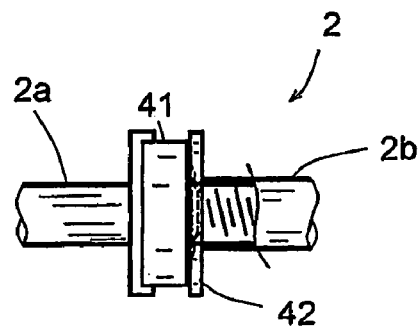
FIG. 11 is a view similar to FIG. 10, after assembly.

FIGS. 10 and 11 show a linking rod 2 of the equipment which comprises:

- a portion of rod 2a including a part 41 with elastically deformable structure and a articulated threaded stud 5, this articulation being identical to that described previously,
- another portion of rod 2b, including a bearing zone 42 against this part 41 and a tapered bore 43 for screwing this portion 2b on the stud 5 in order to clamp the bearing zone 42 against the part 41.

The linking rod 2 may thus also present a certain degree of elastic flexibility.

As shown by the foregoing, the invention provides a vertebral osteosynthesis equipment enabling certain clearance of the connecting part 3, and therefore of the linking rod 2, with respect to the base anchoring portion 6 to the vertebra, to allow limited movements of the vertebrae treated. The stresses exerted on the anchoring bony zones of the anchoring member are thus notably reduced, as well as the risks of over-stresses at vertebral articulations situated on both sides of the vertebral segment treated.

It is obvious that the invention is not limited to the embodiment described above for exemplification purposes but it extends to all the embodiments covered by the claims appended therein. Consequently, one would not depart from the framework of the invention by replacing the wall 27 with a washer of elastic material or with an elastic structure, for instance in the form of a spring.

The invention claimed is:

1. Vertebral osteosynthesis equipment, comprising:
    a polyaxial anchoring member (1) comprising i) a proximal threaded stud (5) and ii) a threaded base portion (6) enabling bony anchoring, the proximal stud articulated with respect to the base portion (6),
    the threaded base portion (6) comprising i) a threaded portion for bony anchoring, ii) a proximal curved wall (17) with a hemispherical proximal form defining a cavity (16), and iii) a collar (18) located between the curved wall (17) and the threaded portion at a location suitable for abutting against a pedicula,
    the proximal stud (5) comprising i) a threaded portion (10), and ii) a distal head (11), the distal head (11) retained in the cavity (16) by the curved wall (17);
    a connecting part (3) engaged on the threaded stud (5),
    the connecting part (3) comprising i) a rounded section (20) connected to ii) two parallel lateral wings (21) with holes for engaging on the proximal stud (5), iii) a circular wall (27) delineating an internal concave spherical face (28) mating with the curved wall (17) of the base portion (6), the circular wall (27) protruding perpendicularly from a lower surface of a lower one of the lateral wings (21), the rounded section for connecting a linking rod (2) to the anchoring member (1); and
    a clamping part (4) screwed on the threaded portion (10) of the proximal stud (5) and clamping against an upper one of the wings (21) of the connecting part (3), wherein,
    the circular wall (27) delineating the internal concave spherical face (28) bears against the curved wall (17) of the base portion (6), an amount of multidirectional backlash of the proximal stud (5) being limited by a lowermost surface of the circular wall (27) abutting against an upper surface of the collar (18), wherein,
    the proximal stud (5) further comprises a collar (12) forming an axial stop surface, and
    the connecting part (3) further comprises a circular cavity (26) shaped to engage with the collar (12) of the proximal stud (5), the circular cavity (26) is engaged with the collar (12) of the proximal stud (5),
    with a longitudinal axis of the stud (2) in alignment with a longitudinal axis of the base portion (6), the stud (2) is in a neutral first position with the lowermost surface of the circular wall (27) held spaced apart from the upper surface of the collar (18) of the base portion (6) at a distance defined by said circular cavity (26) engaged with said axial stop surface of the collar (12) of the stud (5), and
    with the clamping part (4) screwed on the threaded portion (10) of the proximal stud (5) clamping the upper one of the wings (21) against the lower one of the wings (21), the stud (2) is moveable from the first position to a second position with the lowermost surface of the circular wall (27) abutting against the upper surface of the collar (18) of the base portion (6)

2. The vertebral osteosynthesis equipment of claim 1, wherein the circular wall (27) is deformable to dampen movement of the proximal stud (5) with the lowermost surface of the circular wall (27) abutting against the upper surface of the collar (18).

3. The vertebral osteosynthesis equipment of claim 2, wherein,
the circular wall (27) is comprised from i) a deformable part (31) located between a lower one of the two wings (21) and the curved wall (17) of the base portion (6), and ii) a washer (32) located between the lower one of the two wings (21) and the deformable par.

4. The vertebral osteosynthesis equipment of claim 3, wherein, said deformable part (31) is composed of a compressible material.

5. The vertebral osteosynthesis equipment of claim 1, wherein,
adjacent surfaces of the distal head (11) and the curved wall (17) slip against one another during backlash of the proximal stud (5), and
the adjacent surfaces of the distal head (11) and the curved wall (17) include a resistant coating layer capable of resisting slipping movements of the adjacent walls against one another.

6. The vertebral osteosynthesis equipment of claim 5, wherein, the resistant coating layer is a ceramic coating layer.

7. The vertebral osteosynthesis equipment of claim 5, wherein, the resistant coating layer is a titanium nitride coating layer.

8. The vertebral osteosynthesis equipment of claim 1, wherein the circular wall (27) is integral with the lower one of the lateral wings (21)

9. The vertebral osteosynthesis equipment of claim 1, wherein,
adjacent surfaces of the distal head (11) and the curved wall (17) slip against one another during backlash of the proximal stud (5), and
the adjacent surfaces of the distal head (11) and the curved wall (17) include a resistant coating layer capable of resisting slipping movements of the adjacent walls against one another.

10. The vertebral osteosynthesis equipment of claim 9, wherein, the resistant coating layer is a ceramic coating layer.

11. The vertebral osteosynthesis equipment of claim 9, wherein, the resistant coating layer is a titanium nitride coating layer.

12. Vertebral osteosynthesis equipment, comprising:
a polyaxial anchoring member (1) comprising i) a proximal threaded stud (5) and ii) a threaded base portion (6) enabling bony anchoring, the proximal stud articulated with respect to the base portion (6),
the threaded base portion (6) comprising i) a threaded portion for bony anchoring, ii) a proximal curved wall (17) with a hemispherical proximal form defining a cavity (16), and iii) a collar (18) located between the curved wall (17) and the threaded portion at a location suitable for abutting against a pedicula,
the proximal stud (5) comprising i) a threaded portion (10), and ii) a distal head (11), the distal head (11) retained in the cavity (16) by the curved wall (17);
a connecting part (3) engaged on the threaded stud (5),
the connecting part (3) comprising i) a rounded section (20) connected to ii) two parallel lateral wings (21) with holes for engaging on the proximal stud (5), iii) a circular wall (27) delineating an internal concave spherical face (28) mating with the curved wall (17) of the base portion (6), the rounded section for connecting a linking rod (2) to the anchoring member (1); and
a clamping part (4) screwed on the threaded portion (10) of the proximal stud (5) and clamping against an upper one of the wings (21) of the connecting part (3), wherein,
the circular wall (27) delineating the internal concave spherical face (28) bears against the curved wall (17) of the base portion (6), wherein,
the circular wall (27) is deformable to dampen movement of the proximal stud (5) with the lowermost surface of the circular wall (27) abutting against the upper surface of the collar (18),
the circular wall (27) is comprised from i) a deformable part (31) located between a lower one of the two wings (21) and the curved wall (17) of the base portion (6), and ii) a washer (32) located between the lower one of the two wings (21) and the deformable part, the amount of multidirectional backlash of the proximal stud (5) being limited by a lowermost surface of the washer (32) abutting against the upper surface of the collar (18), and
an amount of multidirectional backlash of the proximal stud (5) being limited being limited by a dampening effect provided by the deformable part (31)

13. The vertebral osteosynthesis equipment of claim 12, wherein,
the washer (32) is screwed onto the threaded portion (10) of the proximal stud (5)

14. The vertebral osteosynthesis equipment of claim 12, wherein, said deformable part (31) is composed of a compressible material.

* * * * *